(12) United States Patent
Bishop

(10) Patent No.: US 7,015,445 B2
(45) Date of Patent: Mar. 21, 2006

(54) METHOD FOR OPTIMIZING INSPECTION SPEED IN LOW, AND FLUORESCENT LIGHT APPLICATIONS WITHOUT SACRIFICING SIGNAL TO NOISE RATIO, RESOLUTION, OR FOCUS QUALITY

(75) Inventor: Robert Bishop, Newton, MA (US)

(73) Assignee: Beltronics Inc., Newton, MA (US)

( * ) Notice: Subject to any disclaimer, the term of this patent is extended or adjusted under 35 U.S.C. 154(b) by 0 days.

(21) Appl. No.: 10/737,173

(22) Filed: Dec. 16, 2003

(65) Prior Publication Data
US 2004/0183902 A1 Sep. 23, 2004

Related U.S. Application Data (60) Provisional application No. 60/433,817, filed on Dec. 16, 2002.

(51) Int. Cl.
*G02B 27/64* (2006.01)
(52) U.S. Cl. ............................ 250/201.4; 250/559.46
(58) Field of Classification Search .. 250/201.2–201.4, 250/559.22, 559.45, 559.46; 356/600, 601, 356/606–609; 382/149, 150, 155
See application file for complete search history.

(56) References Cited

U.S. PATENT DOCUMENTS

| 5,672,885 A | * | 9/1997 | Allen et al. ............... 250/559.3 |
| 6,324,298 B1 | * | 11/2001 | O'Dell et al. ............... 382/149 |
| 6,674,058 B1 | * | 1/2004 | Miller ...................... 250/201.4 |
| 2002/0036769 A1 | * | 3/2002 | Shimada et al. .......... 356/237.1 |
| 2003/0053676 A1 | * | 3/2003 | Shimoda et al. ............ 382/145 |
| 2003/0164440 A1 | * | 9/2003 | Czarnelzki et al. ....... 250/201.3 |

* cited by examiner

*Primary Examiner*—David Porta
*Assistant Examiner*—Stephen Yam
(74) *Attorney, Agent, or Firm*—George A. Herbster (57) ABSTRACT

The method for optimizing inspection speed during optical inspection of parts in high, low and fluorescent light applications. There are described autofocus mechanisms and methods optimized for fluorescent and non-fluorescent applications that when combined with a high speed CCD camera and high numerical aperture (NA) optics, achieve superior signal to noise ratio, resolution, and inspection speed performance.

7 Claims, 12 Drawing Sheets

FOCUS BY MINIMIZING WIDTH OF SLIT

WHITE LIGHT IMAGE OF MULTI-LAYERED PART

FIG. 11A

FLUORESCENT IMAGE OF MULTI-LAYERED PART SHOWN ABOVE

METHOD FOR OPTIMIZING INSPECTION SPEED IN LOW, AND FLUORESCENT LIGHT APPLICATIONS WITHOUT SACRIFICING SIGNAL TO NOISE RATIO, RESOLUTION, OR FOCUS QUALITY

CROSS-REFERENCE TO RELATED APPLICATION

This application claims the benefit of Provisional Application No. 60/433,817 filed Dec. 16, 2002.

BACKGROUND OF THE INVENTION

Inspection of electronic parts such as such as wafers, circuit boards, flat panel displays, multi-chip modules, and high-density electronic packages requires sufficient camera signal to noise ratio (S/N) to image the part, a fast camera clock rate to obtain good throughput, and sharp focus with high resolution to insure detection of small defects.

Camera signal output is given by the equation:

$$Cam_{sig} = \frac{Illumination\ Power}{\#\ cam\ pixels} \times OE \times Ref \times Integration\ time \times NA^2 \quad \text{Equation 1}$$

where:
Illumination Power=total illumination power incident on the part
OE=efficiency or transmittance of the optical system Integration time=time duration over which light is collected by the camera
\# cam pixels=the total number of camera pixels
$NA^2$=the numerical aperture of the imaging optics
Ref=the percent of illuminated light reflected off the material for non-fluorescent applications, given by the equation:

$$\frac{reflected\ light\ intensity}{illumination\ light\ intensity}$$

Ref=the percent of fluorescent light emitted by the material in response to the excitation illumination of a different frequency for fluorescent applications; given by the equation:

$$\frac{fluorescent\ emission\ light\ intensity}{Illumination\ excitation\ light\ intensity}$$

The part can be inspected using a single camera or multiple cameras, with each camera viewing a different region of the part, to increase throughput. Each camera may have one or multiple outputs. Therefore, in general terms:
\# Cam pixels=total \# outputs×\# pixels per output The shortest integration time, in Equation 1, is equal to the time required to read the single longest output. If the number of pixels for each output is identical, the integration time can be expressed as:

$$Integration\ time = \frac{\#\ cam\ pixels}{\#\ outputs \times Ck} \quad \text{Equation 2}$$

where Ck=data rate of one output in pixels/second

Substituting Equation 2 into Equation 1 and simplifying terms yields:

$$Cam_{sig} = \frac{Illumination\ Power}{\#\ outputs \times Ck} \times OE \times Ref \times NA^2 \quad \text{Equation 3}$$

The signal to noise ratio of the camera (S/N) is given by the equation:

$$S/N = Cam_{sig0}/N \quad \text{Equation 4}$$

Where N is the electronic noise of the camera.

The time required to readout all the camera data dictates the speed of the inspection. Multiple outputs enable multiple pixels to be read out simultaneously. The effective readout time per pixel referred to as the effective data rate or speed is given by the equation:

$$Speed = Effective\ data\ rate = \#\ outputs \times Ck \quad \text{Equation 5}$$

To summarize:

$$Speed = \#\ outputs \times Ck \quad \text{Equation 6}$$

$$Cam_{sig} = \frac{Illumination\ Power}{\#\ outputs \times Ck} \times OE \times Ref \times NA^2 \quad \text{Equation 7}$$

$$S/N = Cam_{sig}/N \quad \text{Equation 8}$$

Equations 6 and 7 show that the camera signal is inversely proportional to speed. As camera speed increases, signal output decreases because the time during which the pixel collects light is decreased. In applications where illumination power is not limited, power can be increased to compensate for signal loss due the increase in speed. However, in low camera light conditions, which occur in most fluorescent inspection applications or for inspection of low reflectivity parts, both of which correspond to small values of Ref in Equation 7, it may not be feasible, practical, or cost effective to increase illumination power. Fluorescent inspection systems, such as the Orbotech Blazer or Beltronics Mscan III, use expensive lasers as the illumination source. In such systems, it is not cost effective or practical to increase the size of the laser. In extremely fast non-fluorescent scan applications, bulb life also becomes an issue for high power illumination systems. For example, a frequently used 150-watt halogen lamp (model EJV manufactured by Sylvania) or a typical high-pressure mercury vapor lamp (model XXX manufactured by Osram) are only rated for 200 hours of operation at the rated operating voltages. However, if the EJV lamp is operated at a reduced power its life can be greatly extended. Therefore, inspection systems in which camera light is limited because:

fluorescence is used to image the part,
material reflectivity is low, and
illumination intensity is reduced to increase bulb life.

The camera signal can be greatly increased by increasing the numerical aperture (NA) of the imaging optics. Equation 7 states that camera signal strength is proportional to $NA^2$. However, the optical depth of focus (DOF) given by the equation:

$$DOF = \lambda/2 \times NA^2 \quad \text{Equation 9}$$

Figure 1:
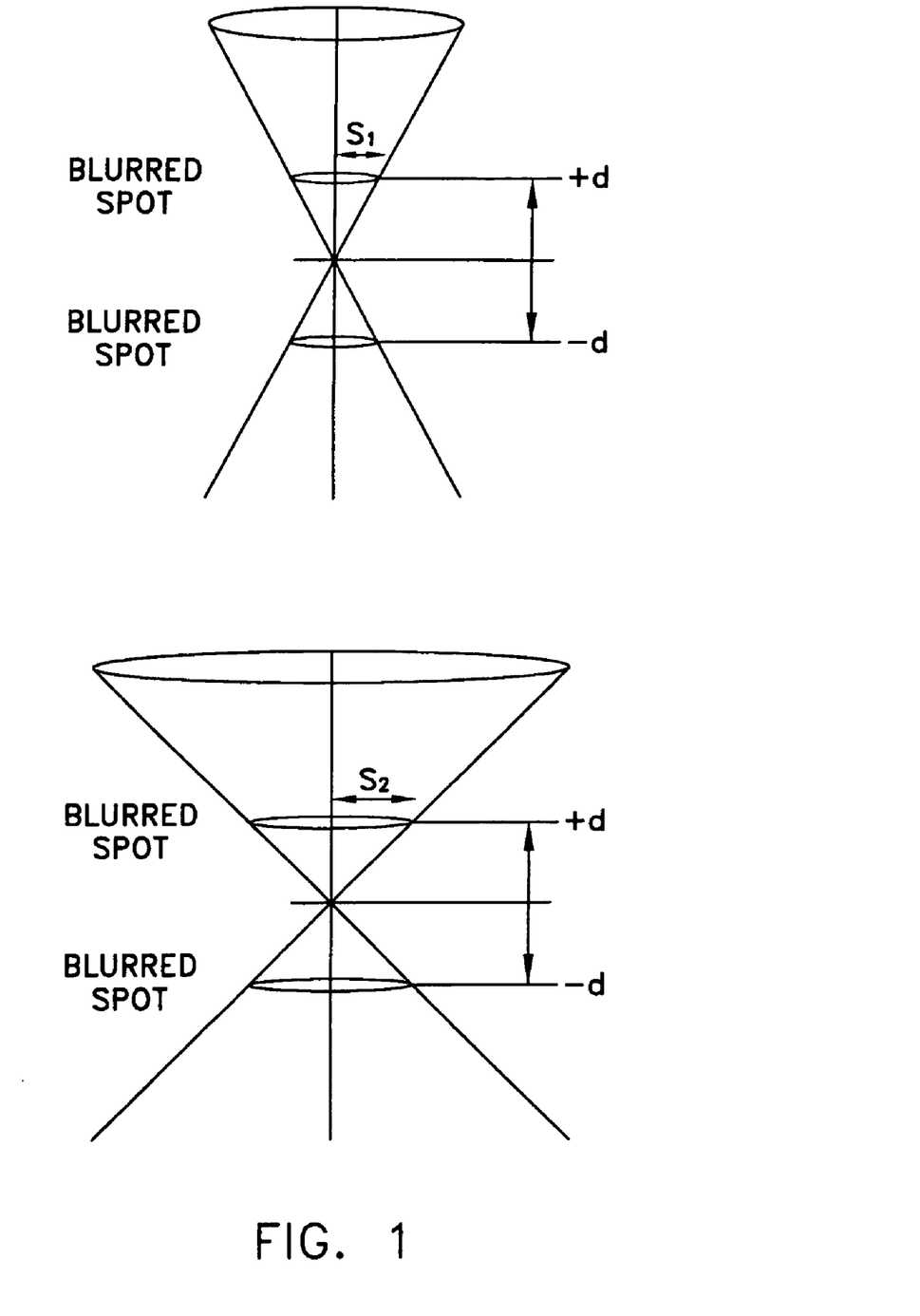
FIGS. 1–4, already described, are diagrammatic views of optical systems useful in understanding the invention.

Where: $\lambda$=Wavelength of light imaged onto the camera new line decreases inversely as $NA^2$ increases. Therefore, if signal strength is increased by using higher NA optics, it may not be possible to maintain focus as the part is scanned. FIG. 1 in the drawings shows the depth of focus ray diagram for a low $S_1$ and high $S_2$ NA lens. The cone angle over which light is collected is given by the equation:

Light Collection Cone Angle $\theta=2\times\sin^1(NA)$.    Equation 10

Table 1 is a list of commercially available lenses from the Zeiss Corporation. The table lists the depth of focus, numerical aperture, resolving power, light collection coefficient, light collection cone angle, working distance magnification and part number for each lens.

TABLE 1

Commercially Available Objective Lenses From Zeiss

| Magnification/ pixel size (microns) | Zeiss Part Number | Numerical Aperture (NA) | Light Collection Coefficient ($NA^2$) | Light Collection Cone Angle (degrees) $\theta = 2 \times \sin^3(NA)$ | Resolving Power for $\lambda = 0.55$ (Microns) $\frac{\lambda}{2 \times NA}$ | Depth of Focus $\lambda = 0.55$ (Microns) $\frac{\lambda}{2 \times NA^2}$ | Working Distance (WD) |
|---|---|---|---|---|---|---|---|
| 1.25×/10.4 | 442300 | 0.035 | 0.0012 | 4.0 | 7.8 | 229 | 3.9 mm |
| 2.5×/5.2 | 442310 | 0.075 | 0.0056 | 8.6 | 3.6 | 49 | 9.4 mm |
| 5×/2.6 | 440320 | 0.15 | 0.0225 | 17 | 1.8 | 12.2 | 13.6 mm |
| 5×/2.6 | — | 0.25 | 0.0625 | 29 | 1.1 | 4.4 | |
| 10×/1.3 | 442832 | 0.25 | 0.0625 | 29 | 1.1 | 4.4 | 12.7 mm |
| 10×/1.3 | 442330 | 0.30 | 0.0900 | 35 | 0.9 | 3.1 | 5.7 mm |
| 20×/0.65 | 442840 | 0.40 | 0.1600 | 47 | 0.7 | 1.7 | 9.8 mm |
| 10×/1.3 | 440135 | 0.50 | 0.2500 | 60 | 0.5 | 1.1 | 2.0 mm |
| 20×/0.65 | 442340 | 0.50 | 0.2500 | 60 | 0.5 | 1.1 | 1.4 mm |

Figure 2:
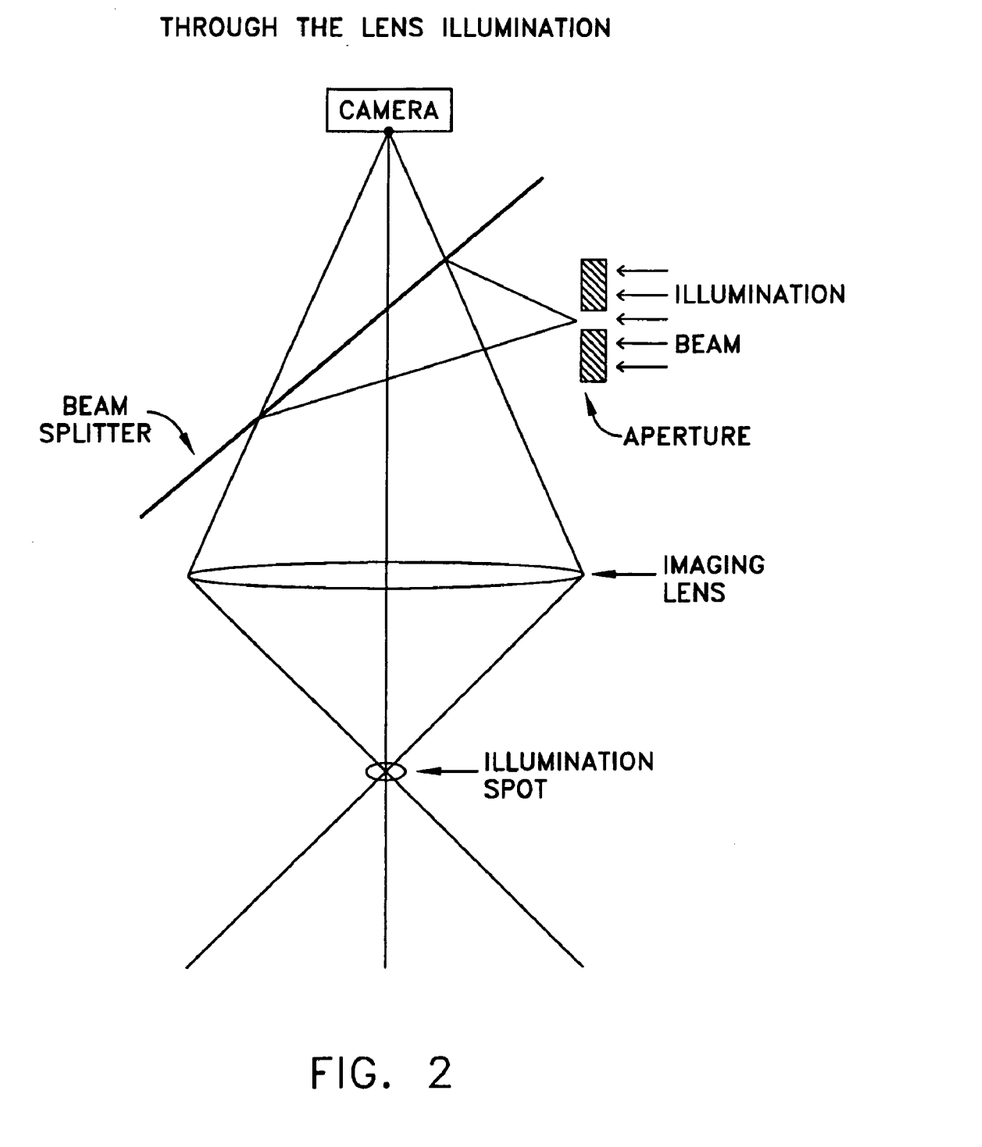

Note that in Table 1 the 1.25X lens with an NA of 0.035 has a depth of focus of 229 microns whereas the 20X lens with an NA of 0.50 only has a depth of focus of 1.1 microns. However, for a through the lens illumination system as shown in FIG. 2, the 20X 0.5 NA lens collects 204 times $(0.5/0.035)^2$ more light than the 1.25X 0.035 NA lens. Unfortunately, unless focus can be maintained to within the 1.1 micron depth of focus, the 20X 0.5 NA lens cannot be used to inspect the part. With current wafers 300 mm in diameter (300,000 microns) and circuit boards or flat panel displays over 700 mm (700,000 microns), maintaining focus to within microns becomes very difficult. Therefore, many inspection systems are forced to use low NA optics, which limits their ability to inspect low reflectivity and fluorescent parts at high speeds. As another example, consider the 5X 0.15 NA and the 5×0.25 NA lens, both with the same magnification. The 0.25 NA lens collects 2.7 times more light than the 0.015 NA lens, but only has a depth of field of 4.4 microns as compared to 12.2 microns. While the 0.25 NA lens enables the system to operate 2.7 times faster than the 0.15 NA lens, this lens can only be used if focus can be maintained to within 4 microns.

Another advantage of high NA optics is higher resolution. Resolving power is given by the equation:

$$Resolving\ power = \frac{\lambda}{2 \times NA} \quad \text{Equation 11}$$

where $\lambda$=wavelength of imaged light.

Therefore, the 1.25X 0.035NA lens can only resolve 7.8 microns as compared to the 20X 0.5 NA lens which can resolve 0.5 microns for $\lambda=0.55$ microns. However, high NA optics cannot be used unless focus can be maintained as the part is scanned.

Therefore, many inspection systems, which do not have auto focus capability, are forced to use low NA optics to maintain focus and are unable to inspect very small features that require high magnification and high resolution.

Two types of auto-focus systems designed for automated inspection applications were introduced by Beltronics in its Mscan II and Mscan III inspection Systems. However, these systems are not suited for high-speed inspection applications because they are slow, with focus time being proportional to the size and flatness of the part. Both auto-focus methods are limited to parts whose surfaces can be topographically expressed as a small number of contiguous planes, as explained with the aid of FIG. 3.

Figure 3:
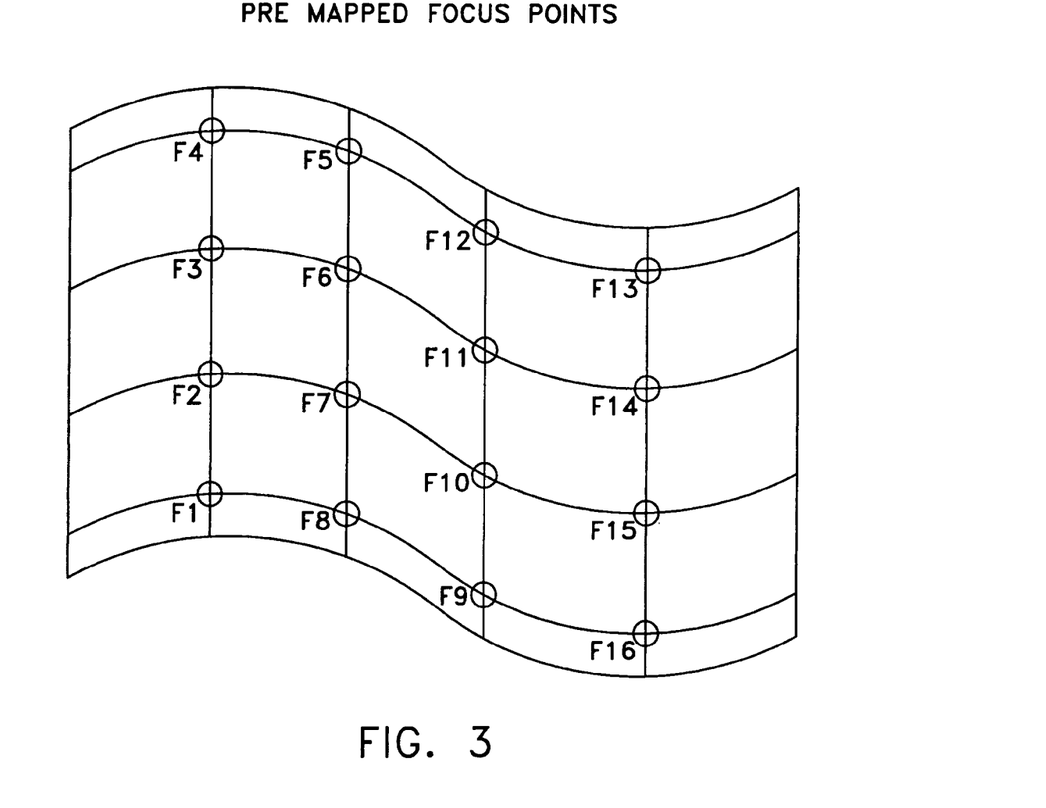

FIG. 3 shows a wavy rolling part with shallow sloped peaks and valleys. Projected onto the part, for the purpose of explaining the focus algorithm, is a grid divided into 16 points, which defines 9 contiguous planes used to model the topology of the part. This group of contiguous planes thus defines a focus map. During the inspection process, the imaging optics is adjusted to track the focus map as a function of the X and Y position of the scanning stage. The computation of this focus map is a slow process, which is performed prior to scanning each part for defects. It involves moving to each point on the grid and computing the Z-axis position that yields optimal focus.

The Beltronics Mscan II defines optimal focus as the Z position that maximizes spatial high frequency information in the image. It is used to inspect grainy textured metal masks. However, this method is not applicable for inspection of smooth homogeneous materials such as circuit board and wafer substrates and resists, which do not contain significant grain, texture, or high frequency information.

Figure 4:
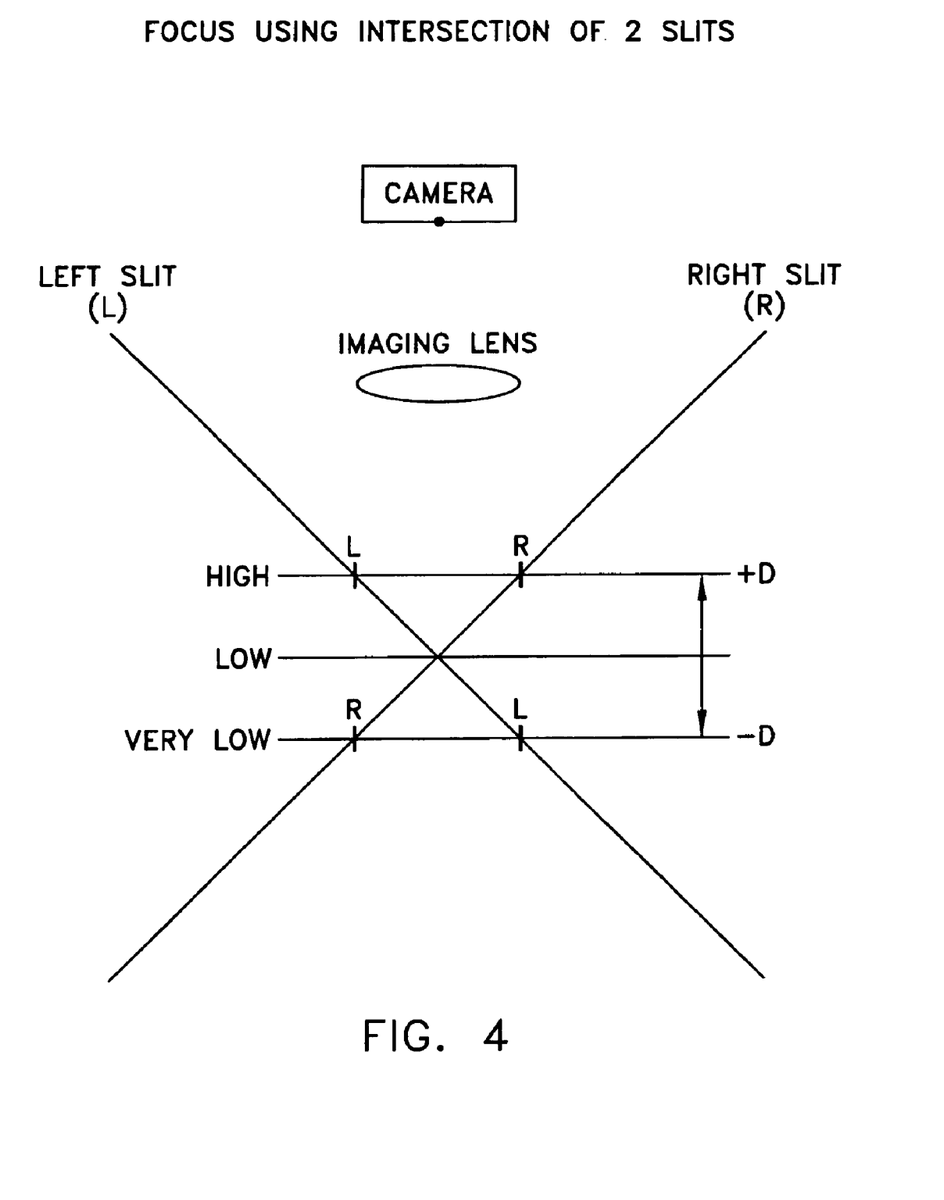

The Mscan III defines optimal focus as the Z position that superimposes two slits onto the surface of the part, one projected from the right, the other from the left, as shown in FIG. 4. This technique has two major limitations When the magnification is high corresponding to a small field of view (FOV), small variations in focus height project the slits totally out of the FOV leaving nothing to focus on, as shown in FIG. 4. When the slits are in the FOV, this technique does not indicate which direction to move along the Z-axis. When the slits are projected out of the FOV, the time required to find optimal focus greatly increases because. the focus algorithm cannot determine in which direction to move.

As an example, let the part be positioned at the Z position labeled "Low" in FIG. 4. No slits are present in the FOV. If the next guess is to move downward such that the optics is focused at position "Very Low" the FOV will still be blank. If the next guess is to move upward such that the optics is now in focus at position "High" the FOV is still be blank. Therefore, one cannot determine in which direction to move and the system hunts up and down until an image of the slits appears in the FOV. As a result of this hunting, the algorithm is easily confused and can become very slow. As parts become larger in size and inherently less flat or as features become smaller requiring higher magnifications for inspection, more points are required in the focus map (FIG. 3) to model the part. This drastically increases the time required to compute the entire focus map such that this computation may take more time than the actual inspection process, which occurs immediately after the map has been calculated.

SUMMARY OF THE INVENTION

Accordingly, it is an object of this invention to provide methods for high speed autofocusing to enable high throughput, automatic inspection of electronic parts.

Another object of the invention is to provide methods for optimizing the inspection of such parts in low light level, high magnification and high resolution applications requiring the use of high NA optics to increase the signal to noise ratio or resolution.

A further object of the invention is to provide methods for decreasing the time required to focus at each grid point in a focus map so as to ensure that a focusing target is always present in the field of view (FOV) to eliminate the hunting problem described at the outset.

Still another object of the invention is to provide apparatus for carrying out the above methods.

Other objects will, in part, be obvious and will, in part, appear hereinafter. The invention accordingly comprises the sequences of steps and the relation of such steps with respect to each of the others and the apparatus embodying the features of construction, combination of elements and arrangement of parts which are adapted to effect such steps, all as exemplified in the following detailed description, and the scope of the invention will be indicated in the claims.

In general, to perform high speed automatic optical inspection of electronic parts such as wafers, circuit boards, flat panel displays, multi chip modules, and high density electronics packages, the inspection system must inspect the part quickly, maintain focus during the scan, maintain a high signal to noise ratio and resolve the smallest of defects. Inspection speed, signal to noise ratio, focus quality and resolution are not independent variables. When inspecting high contrast, high reflectivity materials, fast inspection speeds can usually be achieved at the expense of limiting the optical resolution. However, to inspect low contrast and fluorescent materials when light intensity is minimal, speed must be sacrificed to obtain sufficient signal to noise and maintain focus during the scan.

The present invention optimizes inspection speed in high, low, and fluorescent light applications without sacrificing signal to noise ratio, resolution, or focus quality. It introduces various auto focus mechanisms optimized for fluorescent and non-fluorescent applications that when combined with high speed CCD cameras and high numerical aperture (NA) optics, achieves superior signal to noise ratio, resolution, and speed performance.

Briefly in accordance with my method, a target is projected through an imaging lens onto a part or work piece so that it all positions on the Z-axis, light from the target is present on the part. The width of the target on the partis minimized when the imaging optics is in focus and increases as the part is defocused. Following a focus algorithm, my method computes each focus point on a grid map and then uses these points to create a focus map of contiguous planes to model the surface of the part. Then, the camera or scanning stage is moved during the scanning of this part to track the focus map. Preferably, the part is inspected using a CCD camera in combination with high NA optics (0.05 or larger).

In a first enhancement of the method, to increase focusing speed, a second target may be imaged off axis onto the part to indicate the magnitude and direction of each move to increase the rate of convergence. Once the focus position is sufficiently close to place the second target within the field of view of the imaging lens, the lateral position of that target provides an indication of the direction and magnitude of the move along the Z-axis required to achieve optimal focus. When at optimal focus, the first target will be minimized and the second target will be superimposed on the first target. Then the focus map may be created and the part inspected as before.

The focus time per point may be reduced dramatically by employing a displacement sensor or range finder to measure the distance between the imaging optics and the part or workpiece. This enables the scanning stage to be moved rapidly between successive grid points, pausing only for milliseconds at each grid point to measure the distance to the part.

After all grid locations have been measured, a final focus map is computed and stored in a focus map memory for use during inspection. The camera or stage is moved during scanning of this part to track the focus map. Then, as before, using the CCD camera in combination with high NA optics, the part may be inspected.

In accordance with the foregoing methods, the focus map is created and stored in memory. After the entire map is computed, the part is inspected for defects. Therefore, inspection throughput is proportional to the time required to compute the focus map plus the time required to scan the part. As we shall see, a major improvement in throughput is possible by using the displacement sensor in a look-ahead mode that eliminates the need to compute a focus map prior to each inspection. The look-ahead mode may be used when the workpiece is opaque or when the part contains only one layer such that the displacement sensor only receives reflections from the top layer conductors. It is also possible to utilize this look-ahead autofocusing technique for multilayer parts with transparent or translucent substrates.

As we shall see also, when scanning fluorescent insulators which can be opaque, translucent or transparent, the displacement sensor can be constructed to fluoresce the top layer of the part such that only the top layer is seen by the displacement sensor, effectively eliminating features on the lower layers.

Using my techniques, the inspection of electrical parts may be carried out expeditiously without sacrificing signal to noise ratio, resolution or focus quality.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF ILLUSTRATIVE EMBODIMENTS

1. Focus by Minimizing Width of Target

Figure 5:
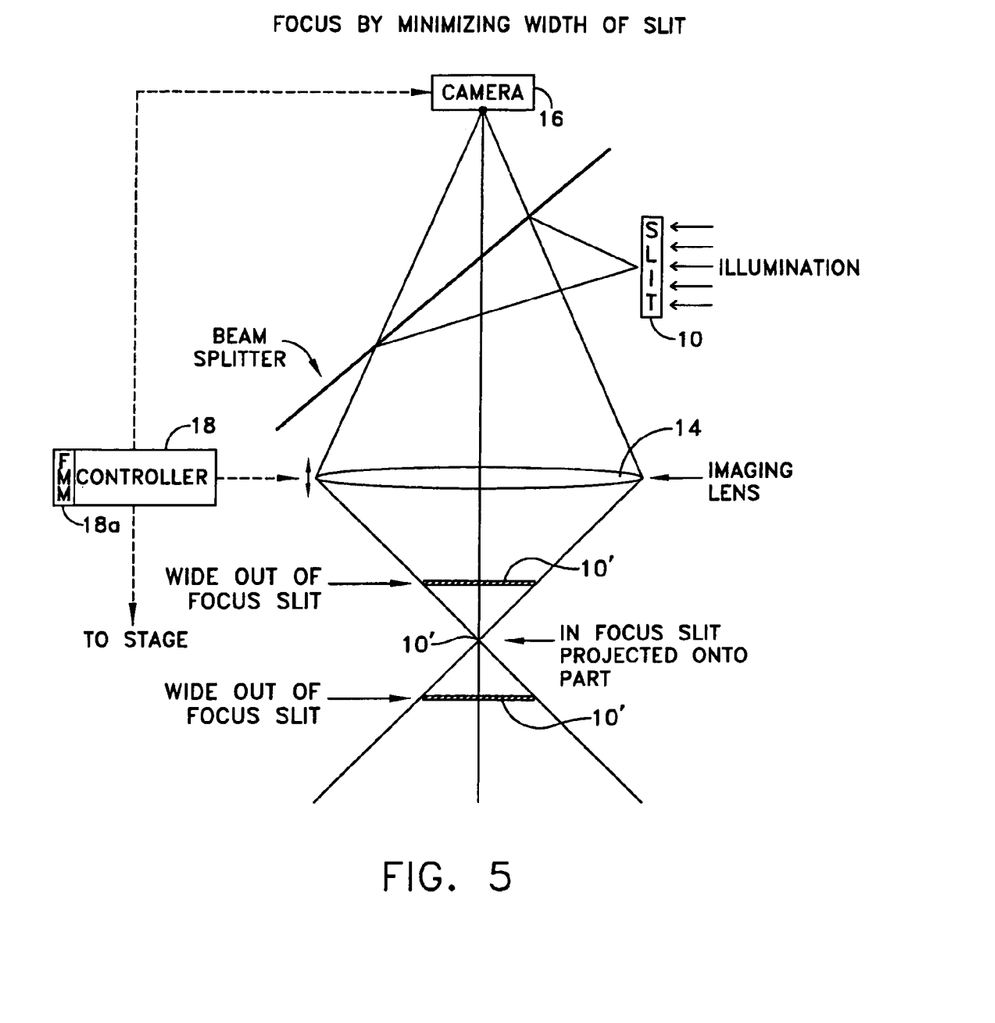
FIG. 5 is a diagrammatic view of a focus illumination apparatus for increasing inspection speed in accordance with a first embodiment of my inspection method.

Referring to FIG. 5, in accordance with this method, a target 10 in the form of a slit is projected by way of a beam splitter 12 through the imaging lens 14 of an inspection camera 16 onto a part or workpiece supported by a scanning stage (not shown). While the illustrated target is a slit, it could just as well be a small dot or an edge. In any event, at all positions along the Z-axis, light from the target 10 is present as shown by the target images 10'. As seen in FIG. 5, when the imaging optics are out of focus in the Z direction, the target image 10' is relatively wide. On the other hand when those optics are in focus, the image 10' has minimum width. Light from the part including the target image is reflected back through lens 14 and the beam splitter 12 to camera 16 which is preferably a CCD camera (see my U.S. Pat. Nos. 5,119,434 and 4,697,088) with high NA (0.05 or larger) optics. Thus, unlike the prior system described above in connection with FIG. 3, a focusing target is always present in the field of view to eliminate the hunting problem.

The operations of the camera 16, including its focussable objective lens 14, and the scanning stage supporting the part are controlled by a controller 18 which includes a focus map memory (FMM) 18a.

In accordance with my method, each target focus point is computed in a grid map in a known way and these points are used to create a focus map of contiguous planes to model the surface of the part as described above in connection with FIG. 3, which map is stored in memory 18a. In other words, the focus map contains the focus value for card focus point in the grid map. During scanning, the scanning stage (or camera) is moved under the control of controller 18 to track the target focus map and the camera lens is focused at each focus point in accordance with the focus value for that point.

Figure 6:
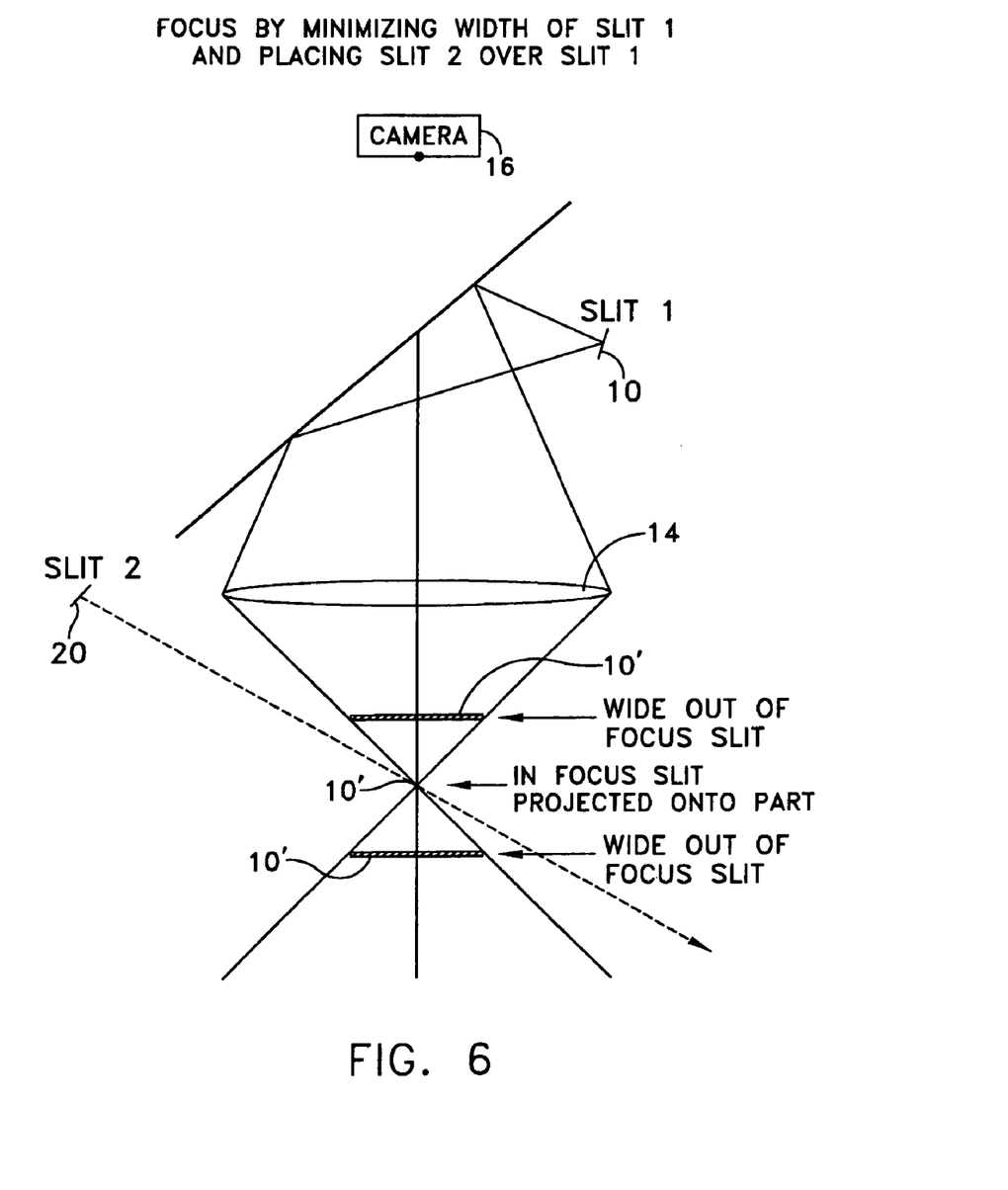
FIG. 6 is a similar view of a second such apparatus for further enhancing inspection speed.

2. Focus by Minimizing Width of One Target And Superimposing a Second Target While the FIG. 5 arrangement eliminates the need to hunt for the target when focusing, the Z-axis position must still be iteratively moved to minimize target size which occurs at optimal focus, to further increase focusing speed, a second target 20 in the form of a second slit may be imaged onto the part as shown in FIG. 6. Preferably, the beam from the second target 20 is inclined at an angle not normal to the part and is off the vertical optical axis as shown in that figure. This beam can either be projected from outside the cone angle of the imaging lens 14 as shown in FIG. 6 or from inside the cone angle if situated with off axis within the rear focal plane of the lens 14. Once the focus position is sufficiently close to place the image of target 20 within the field of view of the lens, the lateral position of the target 20 image on the part provides an indication of the direction and size of the move along the Z-axis required to achieve optimal focus. At the optimal focus position, the target image 10' will have a minimum size and the image of target 20 will be superimposed on image 10'.

Then, using the algorithm described above, the operation computes each focus point on a grid map and uses these target points to create a focus map of contiguous planes to model a surface of the part. Then the camera and scanning stage are moved relatively to track the focus map as before.

3. Incorporation of Range Finder

The techniques that determine optimal focus by converging targets or by optimizing high frequency spatial information are slow, as noted above. Both techniques require that a sequence of images be acquired at sequential Z-axis positions and each image must be analyzed to determine either target position or high frequency content, respectively. For example, if 10 positions are analyzed with an acquisition,and analysis time of 0.5 seconds per image, a total of 5 seconds is required to determine the optimal focus position at each grid point location. I have found that the focus time per point can be dramatically reduced (by a factor of 500 or more) by incorporating a displacement sensor or range finder 19 into the inspection apparatus to measure the actual distance between the camera optics and the part. The displacement sensor under the control of controller 18 enables the scanning stage (or camera) to be moved rapidly between successive grid points, pausing for only milliseconds at each grid point to measure distance to the part.

Figure 7:
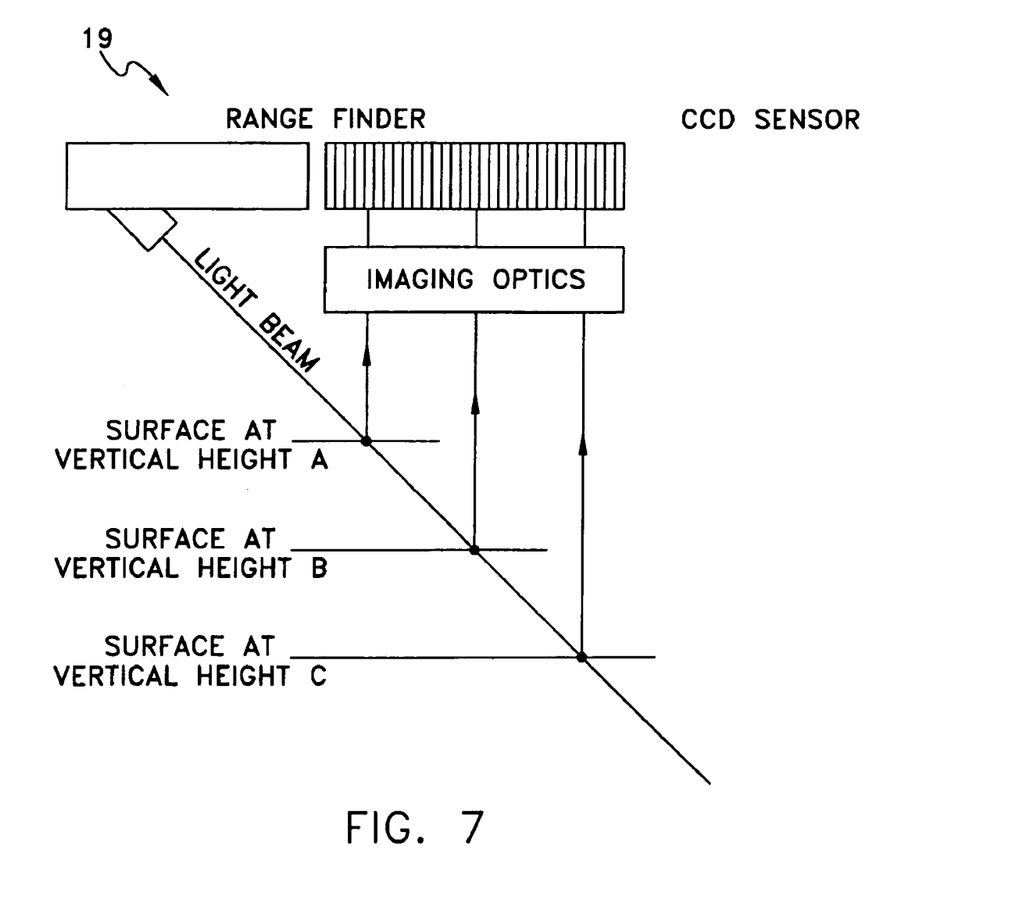
FIG. 7 is a block diagram of a range finder or displacement season for measuring the distance between the focus illumination optics and the workpiece or part.

Operation of the sensor 19 is described with the aid of FIG. 7, which is a block diagram of the model LK series displacement sensor or range finder produced by the Keyence Corporation. FIG. 7 shows an incident light beam reflecting off a part surface positioned at either vertical height A, B, or C. The horizontal position of the CCD pixel illuminated by the reflected beam via imaging optics is a function of the vertical height of the surface. Processing electronics (not shown) converts the illuminated pixel position into a voltage, which correlates to the distance between the optics and that surface. From this voltage measurement, the optimal focus position may be calculated and stored. After all grid locations have been measured, a final focus map may be computed and stored in focus map memory 18a (FIG. 5) for use during inspection.

Figure 8:
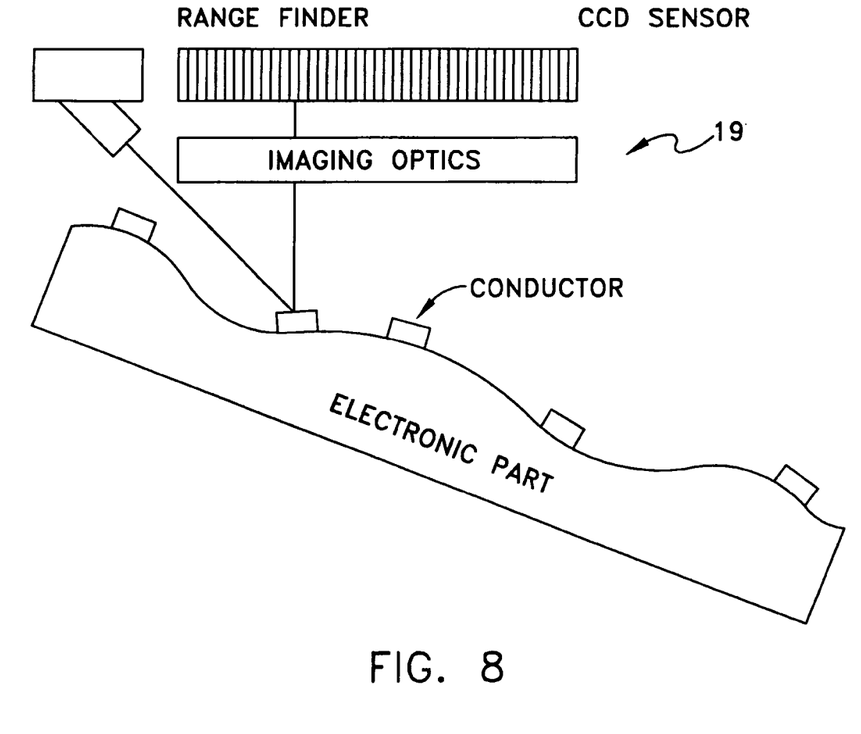
FIG. 8 is a similar diagram showing the FIG. 7 displacement sensor configured to scan a single layer electronic part.

FIG. 8 shows the displacement sensor configured to scan a single layer electronic part consisting of circuit conductor traces on a substrate.

Figure 9:
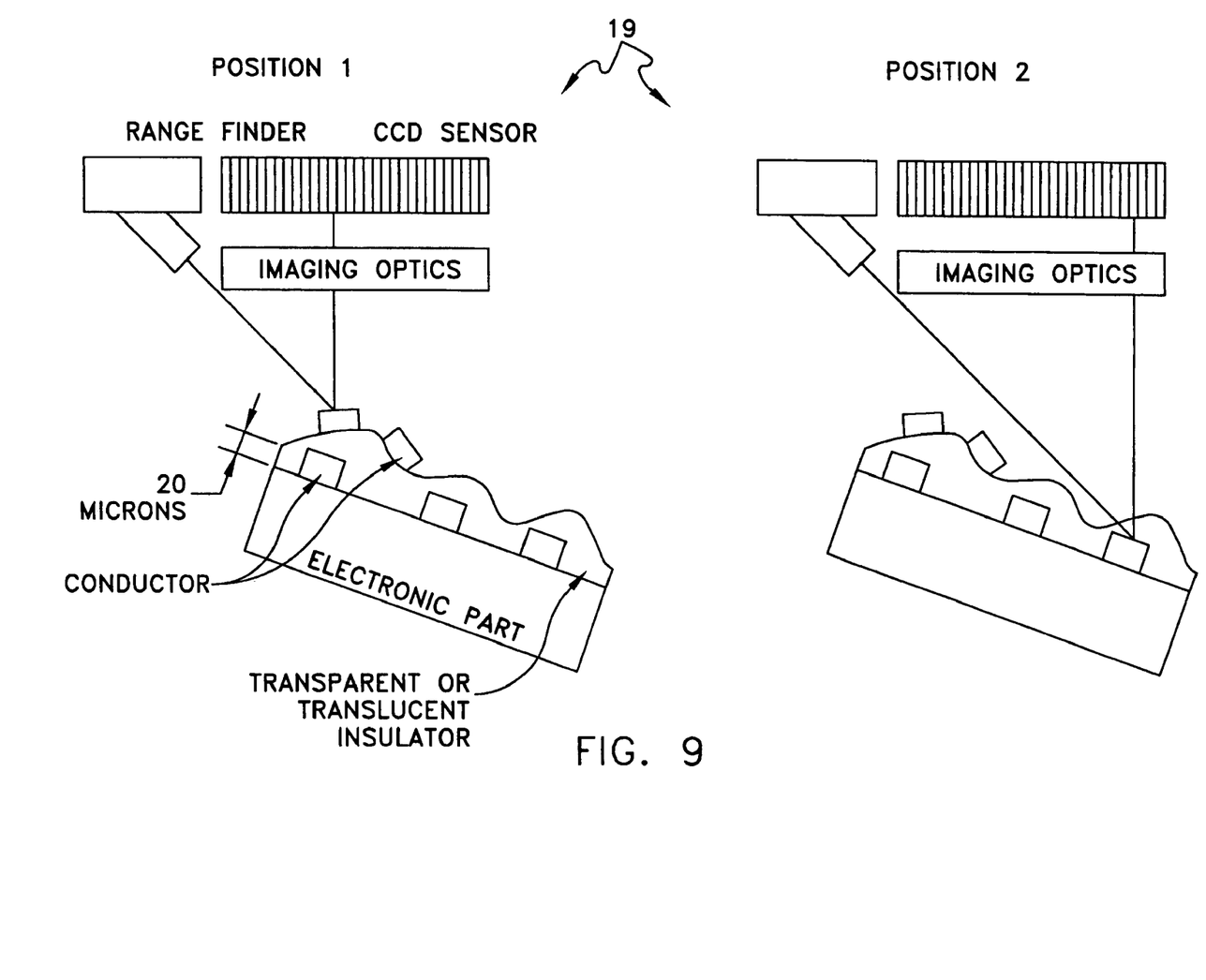
FIG. 9 is a similar view of the sensor configured to scan a multi-layer part.

FIG. 9 shows the displacement sensor configured to scan a multi-layer electronic part.

The locations of the focus map coordinates are typically programmed for a specific design, as part of a one time only set up procedure. To ensure that the topology of the top layer is tracked without complications caused by features on lower layers, or via holes if present, the locations of the focus points are programmed at coordinates which correspond to top layer features.

As before, the focus algorithm of this method computes each focus point on a grid map and these points are used to create a focus map of contiguous planes to model the surface of the part. The camera or stage may be moved during scanning of this part to track the focus map. Thereafter, the CCD camera in combination with high NA optics (0.05 or higher) may be used to inspect the part.

4. Auto Focus Scanning Of Conductor on Opaque Substrates (When The Lower Layer Does Not Show Through)

The focus methods discussed thus far describe means for calculating a focus map. Then after the map is completed the part is inspected for defects. Therefore throughput is proportional to the time required to compute the focus map plus the time required to scan the part. A major improvement in throughput can be achieved by using the displacement sensor in a look ahead mode that eliminates the need to compute a focus map prior to each inspection. We will describe the look ahead mode first for cases where the substrate is opaque or the part only contains one layer, such that the displacement sensor only receives reflections from the top layer conductors. A variation of this method for auto focusing on multilayer parts with transparent or translucent substrates will be described later.

Figure 10:
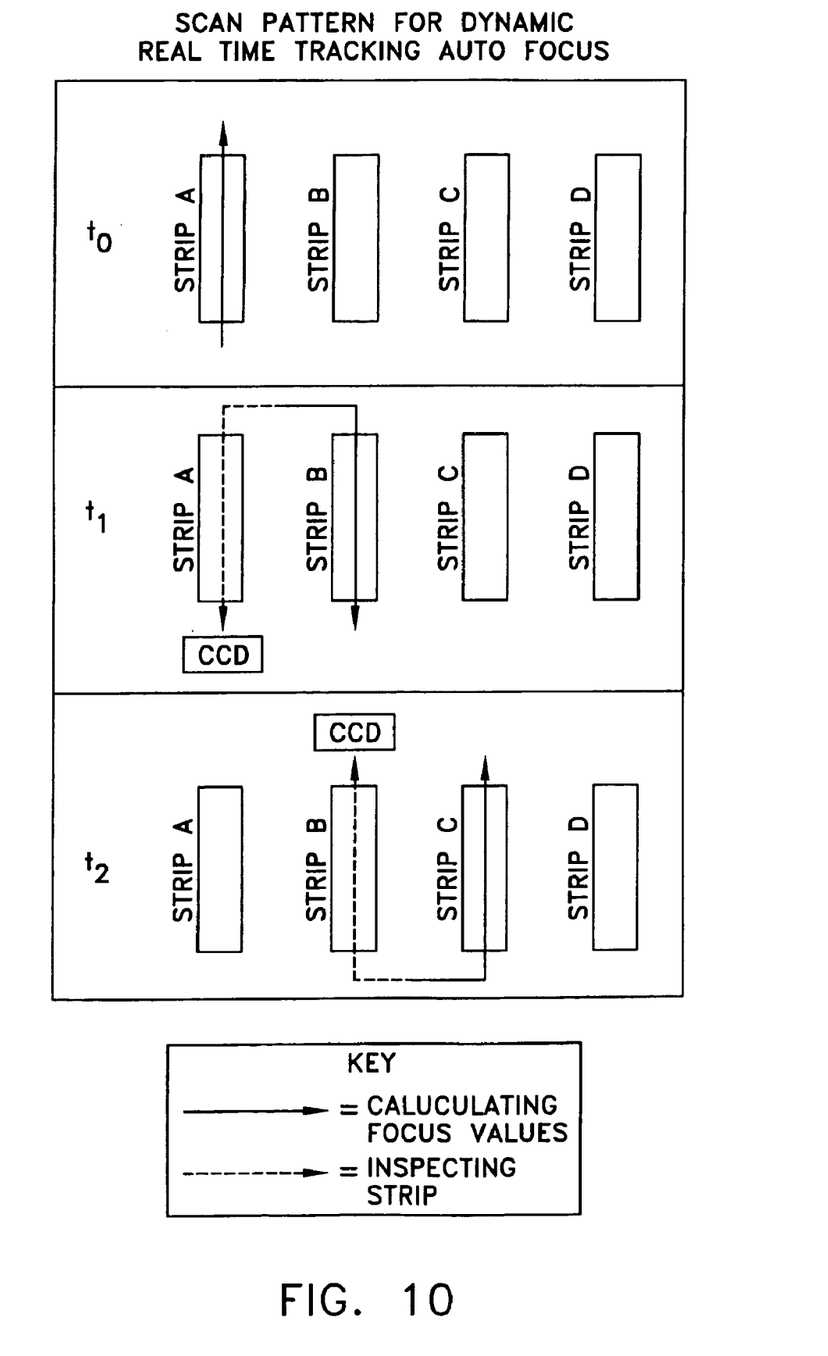
FIG. 10 is a diagrammatic view of a scanning pattern for the displacement sensor operated in a look-ahead mode for a single layer part.

The look ahead mode for the opaque or single layer case is described with the aid of FIG. 10 which shows a part being inspected in a serpentine pattern of contiguous strips. The inspection process begins by scanning the displacement sensor over strip A to compute focus measurements required for inspection of this strip. Each focus measurement may be computed in under 5 milliseconds which enables many focus measurements to be taken within the time required to scan one strip. Immediately thereafter, strip A is inspected using the focus values just computed. Simultaneously, while strip A is being inspected, focus measurements are computed for strip B. Strip B is then inspected simultaneously while focus values are computed for strip C, and so on. As each contiguous strip is inspected, the displacement sensor computes the focus values in temporal and spatial advance of the inspection requiring the focus values.

Performing inspection and focus computations simultaneously, combined with the high density of focus measurements that can be computed using this technique, greatly increases throughput and topology-tracking accuracy as compared to the techniques described in connection with FIGS. 5 to 9.

The focus algorithm of this look ahead mode of operation enables the displacement sensor under the control of controller 18 (FIG. 5) to compute the focus values in temporal and spatial advance of the inspection requiring the focus values. The displacement sensor is positioned ahead of the inspection camera either on the same strip as the camera or looking ahead at a strip to be inspected on a subsequent scan. The displacement sensor is used to compute the focus points and then these points are used to keep the part in focus during inspection. In other words, the displacement sensor computes the focus values in advance of the inspection that requires the focus values. Then the camera moves with the imaging optics or stage, during scanning of each strip, tracking the calculated focus values. This method may be implemented with a CCD camera in combination with high NA optics (0.05 or higher) to inspect the part. This technique is also adapted to create a contour map or focus map of the part using the measured focus values.

5. Auto Focus Scanning of Transparent and Translucent Multilayer Substrates (When The Lower Layer Shows Through)

Figure 11A:
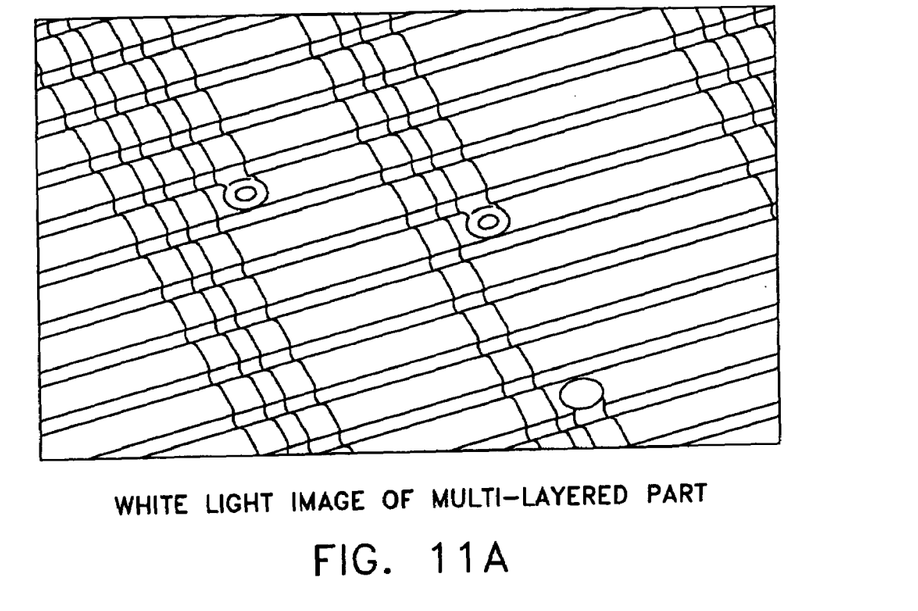
FIG. 11A is a white light image of a multi-layer electronic part that may be inspected in accordance with my methods.

When scanning transparent or translucent multilayer parts as shown in FIG. 11A, opaque parts with via holes, or parts with trenches, the look ahead auto-focus method just described cannot determine which features lie on the top surface of the part and which features lie on lower surfaces. Therefore, the distances provided by the displacement sensor 19 frequently result in a defocused image of the top surface. One method for determining the correct focus distance to the top surface is to extract from the displacement sensor signal regions of high elevation.

A preferred method for accomplishing this task is to divide each look ahead scan strip into small contiguous blocks that correspond in size to the field of view of the imaging lens, as shown in FIG. 11a. For each block, the average distance value for the highest features within that block is computed. These features would correspond to the tops of the metal conductors that lie on the top surface in that figure. These distance values are then used to maintain focus during inspection of the scan strip. This method works well when the density of top layer features within each block is high, as shown in FIG. 11a, because each block or field of view provides many data points for computing the distance to the top layer features. In general, this method for computing the focus distance to the top layer is applicable if a least one top layer feature is present per block. Therefore, when inspecting parts with holes, the block size must be sufficiently large to assure that the hole does not fill the entire block.

If a part contains two layers with only an occasional feature located on the top layer, and one desires to focus on the top layer features, it is possible to compute the average value for the lowest features within each block and to add a constant offset to the measured values that corresponds to the distance between the layers, as a means for keeping the top layer in focus.

In the focus technique of this latest method, a displacement sensor computes focus values in temporal and spatial advance of the inspection requiring the focus values. The displacement sensor is positioned ahead of the inspection camera either on the same strip as the inspection camera or looks ahead at a strip to be inspected during a subsequent scan. The measured focus values may be further processed in controller 18 (FIG. 5) by an elevation detection unit to determine maximum and/or minimum elevation heights of features along the scan. Further, each scanned strip may be divided into small contiguous regions and the average maximum or average minimum elevation within each region is computed. The minimum region size is limited by the maximum data rate of the displacement sensor. Processing the average maximum or average minimum elevation values keeps the part in focus during inspection.

In addition, an average maximum or average minimum elevation detector may be incorporated at the camera system to compute local regions of high or low elevation on the part along each scan strip for the purpose of computing focus points to be used to keep the part in focus during a subsequent inspection.

Preferably, a viewing camera in combination with high NA optics (0.05 or higher) is used to inspect the part. It is also possible to create a contour map or focus map of the part using the measured focus values.

Figure 11B:
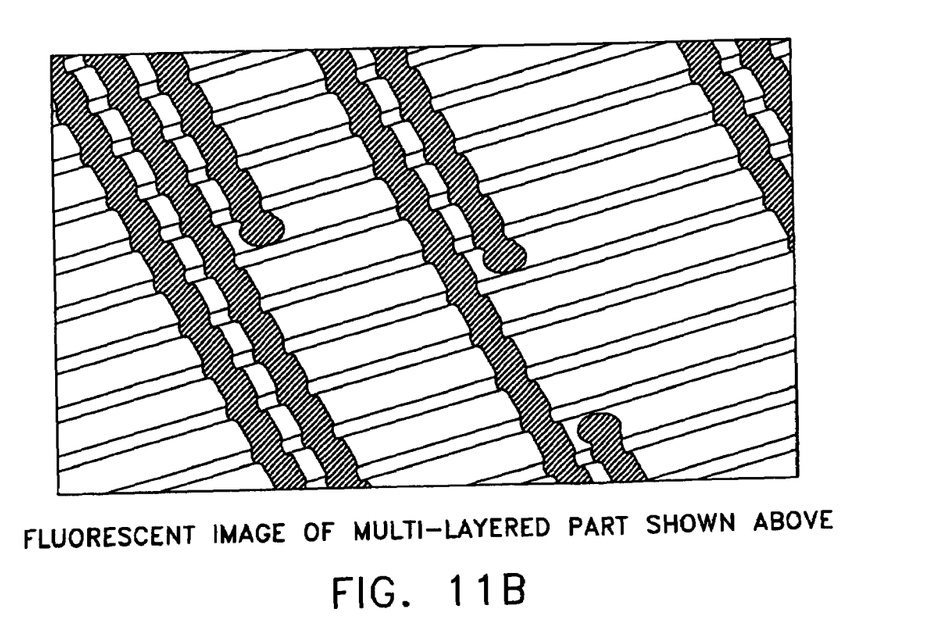
FIG. 11B is a fluorescent image of the same part shown in FIG. 11A.
Figure 12:
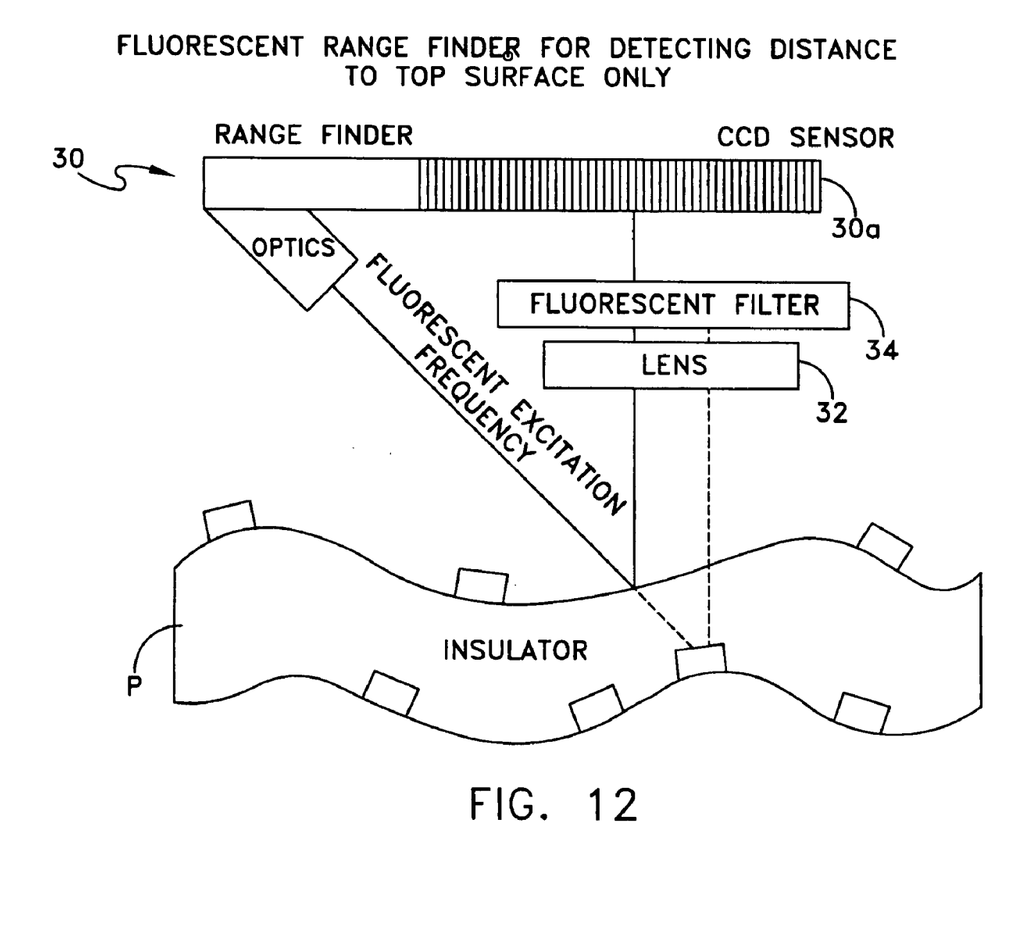
FIG. 12 is a block diagram of a fluorescent range finder for detecting the distance to the top surface only of the part depicted in FIG. 11B.

6. Fluorescent Auto Focus System for Detecting Distance to Part Top Layer Only When scanning fluorescent insulators, which can be opaque, translucent, or transparent as shown in FIG. 11A, the displacement sensor can be constructed to fluoresce the top layer, such that only the top layer is seen by the displacement sensor, effectively eliminating features on the lower layers as shown in FIG. 11B. This is accomplished, as shown in FIG. 12, by emitting an excitation beam from the displacement sensor 30 that excites fluorescent emission from the insulating pattern. The beam can be focused into a target pattern such as a spot, slit, or edge, which is projected onto the part. The fluorescent image thereof is then imaged via a lens 32 and optical filter 34 onto the displacement sensor's linear CCD detector 30a. An optical fluorescent filter 34, which is placed in the image path as shown in FIG. 12, rejects the excitation frequency and only allows the fluorescent frequencies corresponding to the projected pattern to be imaged onto the displacement sensor 30. This underlayer masking effect is described in my U.S. Pat. No. 6,014,209.

In accordance with this method, the displacement sensor 30 preferably computes focus values in temporal and spatial advance of the inspection requiring the focus values, i.e. in a look ahead mode. As shown above, the displacement sensor 30 is positioned ahead of the inspection camera 16 (FIG. 5) either on the same scan strip as the inspection camera or it looks ahead at a strip to be inspected on a subsequent scan. The displacement sensor 30 emits an excitation beam that excites fluorescent emission from the part. The beam projects a pattern or target such as a spot, slit, or edge, onto the part and that fluorescent image is optically converged via lens 32 through filter 34 onto the CCD array 30a of sensor 30. The optical filter 34, rejects the excitation frequency and only allows the fluorescent frequencies corresponding to the projected pattern to be imaged onto the CCD array 30a.

Thus, only the location of the projected pattern in the top layer of the electronic part is imaged. Any signal corresponding to a lower layer is masked or eliminated. The position of the image or image location on the CCD array 30a indicates the height or distance between the displacement sensor 30 and the part or workpiece. That height information may be used to create a focus map of the entire part as described above or a focus map of a scan strip or strips, or to provide real time focus information to maintain focus during inspection of the part.

It will thus be seen that the objects set forth above among those made apparent from the preceding description one efficiently attained and, since certain changes may be made in carrying out the above methods and in the constructions set forth without departing from the scope of the invention, it is intended all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A method for inspecting for defects of a feature disposed as one or more strips over the surface of a part and having a predetermined range of heights, said method comprising the steps of
   providing a camera for optically imaging said feature, said camera being of the type having optics including an objective lens focussable along a Z-axis and with a depth of field that is less than said range of heights and a predetermined field of view;
   providing a displacement sensor fixed relative to said camera and for illuminating a succession of focus points on at least one of said strips to provide at each focus point on indication which correlates to the distance along the Z-axis from said lens to that focus point;
   producing from each indication a focus value for focussing the camera lens when the camera images the corresponding focus point and storing that focus value;
   moving the part relative to the camera and displacement sensor in a scan direction so that the displacement sensor illuminates a leading focus point in the succession of focus points while the camera is imaging a trailing focus point in said succession of focus points, and
   whereby the focus value for each focus point in the succession of focus points is produced in spatial and temporal advance of the imaging by the camera requiring that focus value.

2. The method defined in claim 1 and including the additional step of selecting for the camera a CCD camera with optics having a NA of at least 0.05.

3. The method defined in claim 1 wherein the leading and trailing focus points are on one strip.

4. The method defined in claim 1 the feature includes at least two strips spaced side by side, and
   the leading focus point is on one strip and the trailing focus point is on the other strip.

5. The method defined in claim 1 including the step of positioning the camera and displacement sensor relatively so that the displacement sensor is ahead of the camera in the scan direction.

6. The method defined in claim 1 including the steps of
   forming said feature as side by side strips, and
   positioning the camera and displacement relatively so that the displacement sensor is aimed laterally to the scan direction so that the displacement sensor illuminates one strip while the camera images the other strip whereby the focus value for the focus points on one strip can be produced and stored in advance of the imaging of the one strip by the camera requiring those focus values and while the camera is imaging the other strip.

7. The method defined in claim 1 including the steps of
   forming an image of the part surface of fluorescent material;
   selecting a displacement sensor which projects an illumination pattern of a first frequency that excites fluorescent emission of a second frequency from said surface and which filters out the first frequency so that only light of the second frequency provides said distance indication.

* * * * *